United States Patent
Ferritto et al.

(10) Patent No.: US 6,803,399 B2
(45) Date of Patent: Oct. 12, 2004

(54) SILICONE LIQUID CRYSTALS, VESICLES, AND GELS

(75) Inventors: Michael Salvatore Ferritto, Midland, MI (US); Zuchen Lin, Midland, MI (US); William James Schulz, Jr., Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/465,316

(22) Filed: Jun. 19, 2003

(65) Prior Publication Data

US 2003/0220425 A1 Nov. 27, 2003

Related U.S. Application Data

(62) Division of application No. 09/833,400, filed on Apr. 11, 2001, now Pat. No. 6,608,126.
(60) Provisional application No. 60/256,533, filed on Dec. 18, 2000.

(51) Int. Cl.$^7$ .................. C08K 5/54; C08G 77/388; C08L 83/00

(52) U.S. Cl. .................. 524/267; 524/268; 524/837; 528/28; 528/40; 514/1; 514/553

(58) Field of Search ................ 524/267, 268, 524/837, 266; 528/28, 40; 514/1, 553

(56) References Cited

U.S. PATENT DOCUMENTS

| | | | |
|---|---|---|---|
| 3,046,250 A | 7/1962 | Plueddemann | 260/46.5 |
| 3,655,420 A | 4/1972 | Tichenor et al. | 117/138.8 |
| 4,311,737 A | 1/1982 | Ishizaka et al. | 427/386 |
| 4,891,398 A | 1/1990 | Tanaka et al. | 524/188 |
| 5,525,427 A | 6/1996 | Griswold et al. | 428/447 |
| 5,618,860 A | 4/1997 | Mowrer et al. | 523/421 |
| 5,807,956 A * | 9/1998 | Czech | 528/28 |
| 5,863,988 A | 1/1999 | Hashimoto et al. | 525/105 |
| 5,948,855 A | 9/1999 | Lin et al. | 524/837 |

FOREIGN PATENT DOCUMENTS

| WO | WO 98/32792 | 7/1998 | C08K/3/20 |
|---|---|---|---|

* cited by examiner

Primary Examiner—Margaret G. Moore
Assistant Examiner—Marc S. Zimmer
(74) Attorney, Agent, or Firm—Alan Zombeck

(57) ABSTRACT

Silicone liquid crystals, silicone vesicles, and silicone gels are formed by combining (i) an amine functional silicone or an organic amine compound, (ii) an organic epoxide containing at least two epoxy groups or an epoxy functional silicone containing at least two epoxy groups, and (iii) a fluid such as water, a silicone fluid other than a silicone used in (i) and (ii), and a polar organic compound or nonpolar organic compound other than organic compounds used in (i) and (ii) in which the polar and nonpolar organic compound are present at a concentration to provide a level of solids less than 40 percent by weight based on the weight of (i)–(iii). These silicone liquid crystals, silicone vesicles, and silicone gels are useful in personal care for preparing various skin, hair, and underarm products.

11 Claims, No Drawings

SILICONE LIQUID CRYSTALS, VESICLES, AND GELS

CROSS-REFERENCE TO RELATED APPLICATIONS

This application is a division of U.S. application Ser. No. 09/833,400 filed Apr. 11, 2001 now U.S. Pat. No. 6,608,126 which claims the benefit of Provisional Application Ser. No. 60/256,533, filed on Dec. 18, 2000, in the names of Michael S. Ferritto, William J. Schulz, and Zuchen Lin, entitled "Silicone Elastomer Compositions".

FIELD OF THE INVENTION

This invention is directed to organosilicon compositions, and more particularly to certain silicone liquid crystals, silicone vesicles, and silicone gels.

BACKGROUND OF THE INVENTION

At least as early as 1957, Plueddemann in U.S. Pat. No. 3,046,250 (Jul. 24, 1962) had prepared new polymers in the form of solutions, fluids, viscous fluids, tars, and rubbery solids, by reacting organosilicon epoxides with amine compounds. However, the systems used to prepare these new polymers were anhydrous, and even when a polar solvent such as ethanol was used, it was present at a very high solids level during the reaction, i.e., at least forty-nine percent by weight or more. No new polymers were prepared by Plueddemann in silicone fluids like (i) volatile polydimethylsiloxanes such as hexamethyldisiloxane, octamethyltrisiloxane, and decamethylcyclopentasiloxane; or (ii) nonvolatile polydimethylsiloxanes with a viscosity in the range of 5–10,000 centistoke ($mm^2/s$).

As a result, Plueddemann was not able, and it was not Plueddeman's intent, to prepare any new organosilicon compositions in the form of a silicone liquid crystal, silicone vesicle, or silicone gel, which are the primary focus of the present invention.

BRIEF SUMMARY OF THE INVENTION

The invention relates to silicone liquid crystals, silicone vesicles, and silicone gels, formed by combining (i) an amine functional silicone or an organic amine compound, (ii) an organic epoxide containing at least two epoxy groups or an epoxy functional silicone containing at least two epoxy groups, and (iii) water.

In a second embodiment, silicone gels are formed by combining (i) an amine functional silicone or an organic amine compound, (ii) an organic epoxide containing at least two epoxy groups or an epoxy functional silicone containing at least two epoxy groups, and (iii) a silicone fluid other than the silicone defined in (i) and (ii).

A third embodiment involves forming silicone gels by combining (i) an amine functional silicone or an organic amine compound; (ii) an organic epoxide containing at least two epoxy groups or an epoxy functional silicone containing at least two epoxy groups; and (iii) a polar organic compound or a nonpolar organic compound other than the organic compounds defined in (i) and (ii), in which the polar organic compound or the nonpolar organic compound is present at a concentration to provide a level of solids less than 40 percent by weight based on the total weight of (i)–(iii), where (i) and (ii) are the solids.

One or more active ingredients can be included in any of the above embodiments.

These and other features of the invention will become apparent from a consideration of the detailed description.

DETAILED DESCRIPTION OF THE INVENTION

Silicone liquid crystals and silicone vesicles can be prepared according to this invention by combining:
(i) 0.01–95 percent by weight of an amine functional silicone or an organic amine compound;
(ii) 0.01–95 percent by weight of an organic epoxide or an epoxy functional silicone;
(iii) 0.1–99.98 percent by weight of water; optionally
(iv) 1–30 percent by weight of a surfactant; and optionally
(v) 0.01–50 percent by weight of one or more active ingredients.

Silicone gels can be prepared according to this invention by combining:
(i) 0.1–99.89 percent by weight of an amine functional silicone or an organic amine compound;
(ii) 0.01–99.89 percent by weight of an organic epoxide or an epoxy functional silicone;
(iii) 0.1–99.89 percent by weight of a fluid which can be water, a silicone fluid other than a silicone used in (i) and (ii), a polar organic compound, or a non-polar organic compound; optionally
(iv) 1–30 percent by weight of a surfactant; and optionally
(v) 0.01–50 percent by weight of one or more active ingredients.

In one embodiment, a silicone gel composition is obtained by combining (i) an organic amine compound; (ii) an epoxy functional silicone containing at least two epoxy groups; and (iii) a polar organic compound or a nonpolar organic compound other than the organic compound at defined in (i), in which the polar organic compound or the nonpolar organic compound is present in the composition at a concentration of less than 40 percent by weight based on the total weight of (i)–(iii).

The amine functional polysiloxane used in preparing these compositions has the formula:

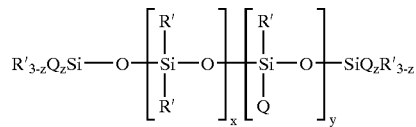

wherein R' denotes an alkyl group of 1 to 30 carbons, an aryl group, an aralkyl group, or an alkaryl group, with the proviso that at least 50 percent of the total number of R' groups are methyl; Q denotes an amine functional substituent of the formula —R"Z wherein R" is a divalent alkylene radical of 3 to 6 carbon atoms and Z is a monovalent radical selected from the group consisting of —$NR_2'''$, and —$NR'''(CH_2)_bNR_2'''$; wherein R'" denotes hydrogen or an alkyl group of 1 to 4 carbons, and b is a positive integer having a value of from 2 to 6; z has a value of 0 or 1; x has an average value of 25 to 3000; y has an average value of 0 to 3,000 when z is 1, y has an average value of 1 to 3,000 when z is 0.

Suitable R' groups are represented by and may be independently selected from among methyl, ethyl, propyl, isopropyl, butyl, isobutyl, phenyl, xenyl, benzyl, phenylethyl, and tolyl, with the proviso that at least fifty percent of the R' groups are methyl.

The alkylene radicals represented by R" may include trimethylene, tetramethylene, pentamethylene, —$CH_2CH(CH_3)CH_2$—, and —$CH_2CH_2CH(CH_3)CH_2$—. Siloxanes where R" is a trimethylene or an alkyl substituted trimethylene radical such as —$CH_2CH(CH_3)CH_2$—, are preferred.

Alkyl groups of 1 to 4 carbon atoms as represented by R''' include methyl, ethyl, propyl, isopropyl, butyl, and isobutyl.

Useful Z radicals include the unsubstituted amine radical —$NH_2$, alkyl substituted amine radicals such as —$NHCH_3$, —$NHCH_2CH_2CH_2CH_3$, and —$N(CH_2CH_3)_2$; and aminoalkyl substituted amine radicals such as —$NHCH_2CH_2NH_2$, —$NH(CH_2)_6NH_2$, and —$NHCH_2CH_2CH_2N(CH_3)_2$.

When z is zero, the silicone polymer has only pendent amine functional substituents in the polymer chain. When z is one, the silicone polymer may have only terminal amine functional substituents or both terminal and pendent amine functional substituents in the polymer chain. Preferably, x may vary from a value of 25 to 500, and y may vary from zero to 100 when z is one and from one to 100 when z is zero. Most preferably, the value of x+y is in the range of about 50 to 1,000.

The amine content, i.e., the number of amine functional groups in the molecule of the amine functional polysiloxane, is generally expressed as mol percent amine, and this is determined according to the relationship y/DP×100, where y is the value of integer y in the above formula for the amine functional polysiloxane, and the Degree of Polymerization (DP) is x+y+2 which indicates the chain length of the amine functional polysiloxane.

Such amine functional polysiloxanes are well known in the art and available commercially from sources such as the Dow Corning Corporation, Midland, Mich. USA.

When it is desired to use an organic amine compound instead of an amine functional polysiloxane, reference may be had to Plueddemann's U.S. Pat. No. 3,046,250 for a detailed list of some representative organic amine compounds, among which are for example, ammonia, diethylene triamine, ethylene diamine, methane diamine, m-phenylene diamine, methylene dianiline, benzohydrazide, guanidine, benzidene sulfone, thioacetamide, piperazine, p-amino benzoic acid, thiosemicarbizide, allanturic acid, p,p'-thiodianiline, p-bromophenyl hydrazine, benzene pentamine, and N,N'-dimethyl ethylene diamine.

Organic epoxides containing at least two epoxy groups, i.e., diepoxides, suitable for use herein include compositions such as ethylene glycol diglycidyl ether, diethylene glycol diglycidyl ether, polyethylene glycol diglycidyl ether, glycerine diglycidyl ether, triglycidyl ether, propylene glycol diglycidyl ether, butanediol diglycidyl ether; 1,2,3,4-diepoxybutane; 1,2,4,5-diepoxypentane; 1,2,5,6-diepoxyhexane; 1,2,7,8-diepoxyoctane; 1,3-divinylbenzene diepoxide; 1,4-divinylbenzene diepoxide; 4,4'-isopropylidene diphenol diglycidyl ether, and hydroquinone diglycidyl ether.

Other polyglycidyl ethers of alkane polyols, polyglycidyl ethers of poly(alkylene glycols), diepoxy alkanes, diepoxy aralkanes, and polyphenol polyglycidyl ethers, can also be used herein.

Two especially preferred organic epoxides containing at least two epoxy groups are shown below, in which n is a positive integer determining the molecular weight of the epoxide.

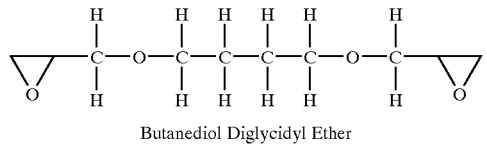

Butanediol Diglycidyl Ether

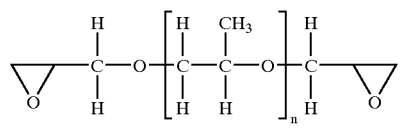

Poly(propylene glycol) Diglycidyl Ether

When it is desirable to use an epoxy functional silicone containing at least two epoxy groups instead of an organic epoxide containing at least two epoxy groups, a suitable epoxy functional silicone of the general structure shown below can be used, in which x represents an integer of one or more.

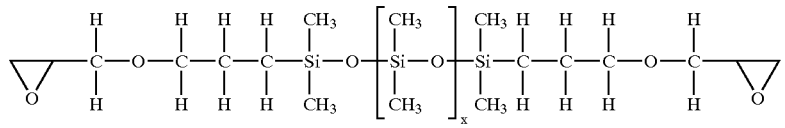

Epoxypropoxypropyl Terminated Polydimethylsiloxane

Such epoxy functional silicones are well known in the art and available commercially from sources such as the Dow Corning Corporation, Midland, Mich. USA. Typically, such silicones have a viscosity ranging from 1 to about 200 centistoke ($mm^2/s$) and molecular weights of about 300–6,000.

If desired, organic epoxides and epoxy functional silicones containing a single epoxy group can be included as an additional component, in order to control the cross link density and the overall molecular weight of the silicone gel.

U.S. Pat. No. 5,948,855 (Sep. 7, 1999) contains an extensive lists of appropriate silicone fluids which can be used, among which are for example, (i) volatile polydimethylsiloxanes such as hexamethyldisiloxane, octamethyltrisiloxane, and decamethylcyclopentasiloxane; and (ii) nonvolatile polydimethylsiloxanes. These volatile and nonvolatile polydimethylsiloxanes include silicone fluids having a viscosity ranging from 0.65 to 10,000 centistoke ($mm^2/s$).

U.S. Pat. No. 5,948,855 also contains an extensive list of nonpolar organic compounds which can be used, among which are fragrances such as musk and myrrh, and mixtures thereof. In addition, nonpolar organic compounds such as natural oils derived from animal, vegetable, or mineral sources are also suitable. Most preferred are modern cosmetic oils known to be safe for cosmetic purposes such as almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

Some polar organic compounds which can be used are monohydroxy alcohols such as ethyl alcohol and isopropyl alcohol; diols and triols such as propylene glycol, 2-methyl-1,3-propane diol $HOCH_2CH(CH_3)CH_2OH$, 1,2-hexanediol $CH_3(CH_2)_3CH(OH)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols, among which are PPG-14 butyl ether $C_4H_9[OCH(CH_3)CH_2]_{14}OH$.

The surfactant can be a nonionic, cationic, anionic, or a mixture of such surfactants. Most preferred are organic nonionic surfactants, but the nonionic surfactant can be one containing a silicon atom. Most preferred are alcohol ethoxylates $R2-(OCH_2CH_2)_cOH$, most particularly fatty alcohol ethoxylates. Fatty alcohol ethoxylates typically contain the characteristic group $-(OCH_2CH_2)_cOH$ which is attached to fatty hydrocarbon residue R2 which contains about eight to about twenty carbon atoms, such as lauryl ($C_{12}$), cetyl ($C_{16}$) and stearyl ($C_{18}$). While the value of "c" may range from 1 to about 100, its value is typically in the range of 2 to 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under such names as ALFONIC®, BRIJ, GENAPOL®, LUTENSOL, NEODOL®, RENEX, SOFTANOL, SURFONIC®, TERGITOL®, TRYCOL, and VOLPO.

One especially useful nonionic surfactant is polyoxyethylene (23) lauryl ether, a product sold under the name BRIJ 35L by ICI Surfactants, Wilmington, Del. It has an HLB of about 16.9.

Cationic surfactants useful in the invention include compounds containing quaternary ammonium hydrophilic moieties in the molecule which are positively charged, such as quaternary ammonium salts represented by $R3R4R5R6N^+X^-$ where R3 to R6 are alkyl groups containing 1–30 carbon atoms, or alkyl groups derived from tallow, coconut oil, or soy; and X is halogen such as chlorine or bromine, or X can be a methosulfate group. Most preferred are dialkyldimethyl ammonium salts represented by $R7R8N^+(CH_3)_2X^-$, where R7 and R8 are alkyl groups containing 12–30 carbon atoms, or alkyl groups derived from tallow, coconut oil, or soy; and X is halogen or a methosulfate group. Monoalkyltrimethyl ammonium salts can also be employed, and are represented by $R9N^+(CH_3)_3X^-$ where R9 is an alkyl group containing 12–30 carbon atoms, or an alkyl group derived from tallow, coconut oil, or soy; and X is halogen or a methosulfate group.

Representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under such names as ADOGEN, ARQUAD, SERVAMINE, TOMAH, and VARIQUAT.

Examples of anionic surfactants include sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate $CH_3(CH_2)_{11}OSO_3Na$; ether sulfates having alkyl groups of eight or more carbon atoms; and alkylaryl sulfonates having one or more alkyl groups of eight or more carbon atoms.

Commercial anionic surfactants useful in this invention include triethanolamine linear alkyl sulfonate sold under the name BIO-SOFT N-300 by the Stepan Company, Northfield, Ill.; sulfates sold under the name POLYSTEP by the Stepan Company; and sodium n-hexadecyl diphenyloxide disulfonate sold under the name DOWFAX 8390 by The Dow Chemical Company, Midland, Mich.

The liquid crystals, vesicles, and gels, prepared according to the invention may contain one or more active ingredients in one or more of their phase(s). Some representative aqueous and polar organic compound soluble active ingredients are (i) Vitamins, (ii) drugs including activated antiperspirant salts such as aluminum chlorohydrate and aluminum-zirconium trichlorohydrate, or (iii) α-hydroxy acids such as glycolic acid, lactic acid, tartaric acid, and citric acid, i.e., fruit acids. U.S. Pat. No. 5,948,855 contains an extensive list of aqueous and polar organic compound soluble Vitamins and drugs which can be used, among which are Vitamin C, Vitamin $B_1$, Vitamin $B_2$, Vitamin $B_6$, Vitamin $B_{12}$, niacin, folic acid, biotin, and pantothenic acid.

U.S. Pat. No. 5,948,855 also contains an extensive list of nonpolar oil soluble active ingredients which can be carried in a phase(s) of the silicone fluid or nonpolar organic compound, such as vitamins and drugs among which are Vitamin $A_1$, RETINOL, $C_2$–$C_{18}$ esters of RETINOL, Vitamin E, TOCOPHEROL, esters of Vitamin E, RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, TOCOPHERYL SUCCINATE, and mixtures thereof.

Other common types of active ingredients can also be included in any phase(s), if desired, such as a fragrance or a sunscreen, i.e., an UV absorber/UV light stabilizer.

Silicone liquid crystals, silicone vesicles, and silicone gels of the invention can be prepared at room temperature using simple propeller mixers, turbine-type mixers, Brookfield counter-rotating mixers, or homogenizing mixers. No special equipment or processing conditions are generally required. Often, simple hand shaking is sufficient. Heat facilitates their formation, and so these compositions can be prepared at temperatures ranging from 25–100° C.

EXAMPLES

The following examples are set forth in order to illustrate this invention in more detail. In these examples, the amine functional silicone that was used had a structure generally corresponding to the formula set forth above, in which R', x, y, z, and Q, are shown in Table 1.

TABLE 1

| Example | R' | x | y | z | Q |
|---|---|---|---|---|---|
| 1 | $CH_3$ | 269.5 | 117.5 | 0 | $-CH_2CH(CH_3)CH_2NHCH_2CH_2NH_2$ |
| 2 | $CH_3$ | 269.5 | 117.5 | 0 | $-CH_2CH(CH_3)CH_2NHCH_2CH_2NH_2$ |
| 3 | $CH_3$ | 89.9 | 8.0 | 0 | $-CH_2CH(CH_3)CH_2NHCH_2CH_2NH_2$ |
| 4 | $CH_3$ | 269.5 | 117.5 | 0 | $-CH_2CH(CH_3)CH_2NHCH_2CH_2NH_2$ |
| 5 | $CH_3$ | 85.0 | 15.0 | 0 | $-CH_2CH_2CH_2NH_2$ |
| 6 | $CH_3$ | 85.0 | 15.0 | 0 | $-CH_2CH_2CH_2NH_2$ |
| 7 | $CH_3$ | 85.0 | 15.0 | 0 | $-CH_2CH_2CH_2NH_2$ |
| 8 | $CH_3$ | 85.0 | 15.0 | 0 | $-CH_2CH_2CH_2NH_2$ |
| 9 | $CH_3$ | 269.5 | 117.5 | 0 | $-CH_2CH(CH_3)CH_2NHCH_2CH_2NH_2$ |
| 10 | $CH_3$ | 269.5 | 117.5 | 0 | $-CH_2CH(CH_3)CH_2NHCH_2CH_2NH_2$ |
| 11 | $CH_3$ | 269.5 | 117.5 | 0 | $-CH_2CH(CH_3)CH_2NHCH_2CH_2NH_2$ |

Example 1

0.5099 g of an amine functional silicone having the characteristics as defined in Table 1, 0.1435 g of 1,4-butanediol diglycidyl ether, and 4.7143 g of $H_2O$ were weighed in a vial. The vial was placed in an 80° C. oven for 2 hours resulting in a cloudy solution. Optical microscopy confirmed that the particles were birefringent indicating the formation and existence of vesicles.

Example 2

0.5337 g of an amine functional silicone having the characteristics as defined in Table 1, 0.6446 g of polyethylene glycol diglycidyl ether having a molecular weight of about 526, 0.3113 g of BRIJ 35L nonionic surfactant, and 5.0908 g of $H_2O$ were weighed into a vial. The vial was placed in an 80° C. oven for 2 hours resulting in the formation of a clear gel with a blue tint. Optical microscopy confirmed the existence and formation of a lamellar liquid crystal.

Example 3

First, 3.2685 g of an amine functional silicone having the characteristics as defined in Table 1, 6.1542 g of a one percent salt solution containing 10 percent by weight of sodium dodecyl sulfate anionic surfactant, and 22.0164 g of $H_2O$ were weighed into a vial. Second, 10.0905 g of the mixture in the vial; 0.5027 g of PARSOL MCX, a UV absorber/UV light stabilizer which is 2-ethylhexyl-p-methoxy cinnamate, sold by Givaudan-Roure, Clifton, N.J.; and 0.1684 g of polypropylene glycol diglycidyl ether having a molecular weight of about 640; were placed in another vial. This vial was placed in an 80° C. oven for 4 hours resulting in the formation of a cloudy dispersion. Optical microscopy confirmed that the particles observed were vesicles. This example also demonstrates the use of a polymerized vesicle to entrap an active ingredient.

Example 4

0.5060 g of an amine functional silicone having the characteristics as defined in Table 1, 1.0058 g of polyethylene glycol diglycidyl ether having a molecular weight of about 526, 0.4970 g of BRIJ 35L nonionic surfactant, and 8.2702 g of $H_2O$ were weighed into a vial. The vial was placed into an 80° C. oven for 2 hours resulting in the formation of a clear gel.

Example 5

1.5165 g of an amine functional silicone having the characteristics as defined in Table 1, 0.5000 g of 1,4-butanediol diglycidyl ether, 6.0165 g of a water solution containing 20 percent by weight of sodium dodecyl sulfate anionic surfactant, and 0.7154 g of 2-methyl-1,3-propanediol which was used as a cosolvent, were weighed into a vial. The vial was placed in an 80° C. oven for 2 hours resulting in the formation of a clear gel.

Example 6

2.1278 g of an amine functional silicone having the characteristics as defined in Table 1, 2.2221 g of 1,4-butanediol diglycidyl ether, 5.0538 g of a water solution containing 20 percent by weight of sodium dodecyl sulfate anionic surfactant, and 1.0193 g of decamethylcyclopentasiloxane, were weighed into a vial. The vial was placed in an 80° C. oven for 2 hours resulting in the formation of a clear gel. This example also demonstrates the inclusion of a volatile cyclic polydimethylsiloxane $[(CH_3)_2SiO]_5$ in a water based gel.

Example 7

1.5452 g of an amine functional silicone having the characteristics as defined in Table 1, 6.1404 g of a water solution containing 20 percent by weight of sodium dodecyl sulfate anionic surfactant, 0.9542 g of polyethylene glycol diglycidyl ether having a molecular weight of about 200, 0.5100 g of 1,4-butanediol diglycidyl ether, and 0.1256 g of a fragrance sold under the name JOOP, were weighed into a vial. The vial was placed in an 80° C. oven for one hour resulting in the formation of a clear gel having a yellow tint. This example also demonstrates the use of a gel to entrap an active ingredient.

Example 8

Into a reaction vial were placed 25.5 g of decamethylcyclopentasiloxane, 0.70 g of 1,4-butanediol diglycidyl ether, and 3.80 g of an amine functional silicone with a degree of polymerization of 100, containing about 15 mole percent of aminopropyl units, and having the characteristics as defined in Table 1. The mixture was stirred until homogeneous and placed in a 70° C.±5° C. bath for 2 hours. Upon removal from the bath, a cloudy gel had been obtained.

Example 9

5.40 g of an amine functional silicone having the characteristics as defined in Table 1, 4.60 g of 1,4-butanediol diglycidyl ether, and 40.25 g of propylene glycol were weighed into a vial. The vial was placed in an 80° C. oven for 2 hours resulting in the formation of a clear gel.

Example 10

1.0901 g of an amine functional silicone having the characteristics as defined in Table 1, 0.9350 g of 1,4-butanediol diglycidyl ether, and 8.0942 g of an antiperspirant salt active, were weighed into a vial. The antiperspirant salt active used in this example was a propylene glycol solution containing about 32 percent by weight of an aluminum-zirconium tetrachlorohydrex glycine complex. The vial was placed in an 80° C. oven for 2 hours resulting in the formation of a clear gel.

Example 11

2.3964 g of an amine functional silicone having the characteristics as defined in Table 1, 1.9428 g of 1,4-butanediol diglycidyl ether, and 6.0644 g of PPG-14 butyl ether were weighed in a vial. The vial was placed in an 80° C. oven for 2 hours resulting in the formation of a clear gel.

It should be noted that one of the benefits derived from crosslinked silicone liquid crystals and silicone vesicles prepared according to this invention is their structural integrity against changes in such parameters as temperature, and the presence or absence of other components such as water, surfactants, and oils. Another benefit is their reduced permeability for entrapped active ingredients by the formation of more compact structures following crosslinking.

Compositions according to this invention are useful in personal care, for example, in preparing antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair sprays, mousses, permanents, depilatories, cuticle coats, and temporary or permanent hair colorants. In cosmetics, they can be added to make-ups, color cosmetics, foundations, blushes, lipsticks, eyeliners, mascara, oil removers, color cosmetic removers, and powders. In such applications, the compositions may include oil soluble, polar solvent soluble, and water soluble ingredients such as vitamins as noted above.

These compositions are also capable of functioning as carriers for pharmaceuticals, biocides, herbicides, pesticides, and other biologically active substances; and they have utility as additives for cellulosic or synthetic nonwoven carrier substrates used in wet-like cleansing wipes such as wet-wipes, tissues, and towels, marketed generally for personal hygiene and household cleaning tasks.

Since the exact nature of the organosilicon compositions described in this invention is largely dependent upon components used in their prepartion, it is difficult to specify the precise nature of their structure. However, it is believed that these organosilicon compositions would have approximate structures generally corresponding to one of the following Formulas I or II.

Thus, the organosilicon composition can have a structure defined by the formula:

Formula I

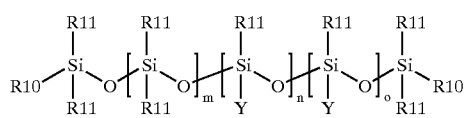

In Formula I, R11 is an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; or an aralkyl group such as benzyl, phenylethyl, or 2-phenylpropyl. R10 can be the same as R11, or R10 can be Y.

Y is the structure

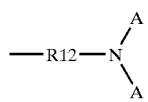

such as the group

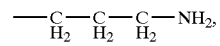

or Y can have the structure

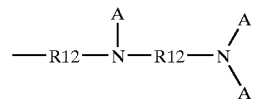

such as the group

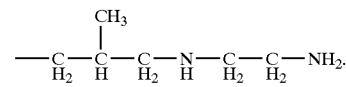

The value of m in Formula I is 1–5,000. The value of n and o in Formula I is 1–200.

R12 in structure Y shown above represents a divalent alkyl group such as methylene, ethylene, propylene, or butylene; a divalent aryl group such as phenylene, biphenylene, naphthylene, or anthracylene; a divalent alkaryl group such as tolylene or xylylene; or a divalent aralkyl group such as benzylene, phenylethylene, or 2-phenylpropylene.

The A constituent in structure Y represents an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; an aralkyl group such as benzyl, phenylethyl, or 2-phenylpropyl; or A can be a hydrogen atom.

In addition, A can be a group such as

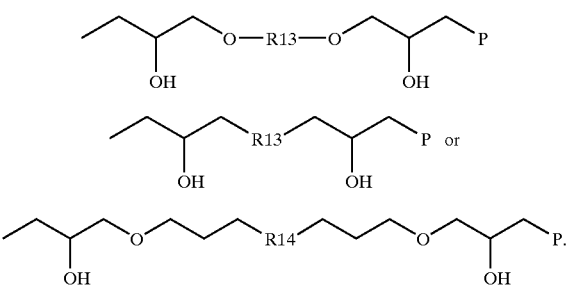

In groups A above, P represents the structure

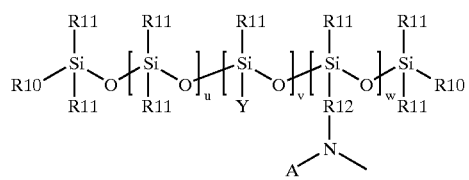

in which u is 1–5,000; v and w are 1–200; and R10, R11, Y, and A, are the same as previously defined.

R13 represents a divalent alkyl group such as methylene, ethylene, propylene, or butylene; a divalent aryl group such as phenylene, biphenylene, naphthylene, or anthracylene; a divalent alkaryl group such as tolylene or xylylene; or a divalent aralkyl group such as benzylene, phenylethylene, or 2-phenylpropylene.

In addition, R13 can be a poly(alkylene oxide) group such as poly(ethylene oxide), a representative example of which is —(CH₂CH₂O)₁₋₃₀—, poly(propylene oxide), a representative example of which is —(CH₂CHCH₃O)₁₋₃₀—, or a mixed poly(ethylene oxide/propylene oxide) group.

Further, R13 can be a structure such as

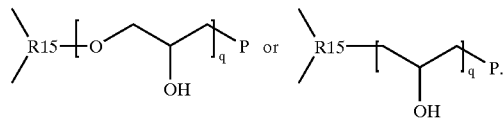

R15 represents a divalent alkyl group such as methylene, ethylene, propylene, or butylene; a divalent aryl group such as phenylene, biphenylene, naphthylene, or anthracylene; a divalent alkaryl group such as tolylene or xylylene; or a divalent aralkyl group such as benzylene, phenylethylene, or 2-phenylpropylene; a poly(alkylene oxide) group such as poly(ethylene oxide), poly(propylene oxide), or a mixed poly(ethylene oxide/propylene oxide); q is 0–60; and P is the same as previously defined.

The R14 group shown in the groups A above is representative of structure such as

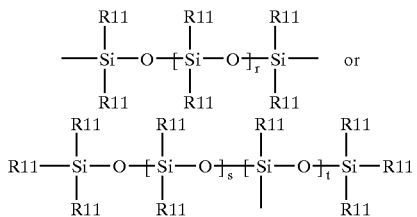

where r and s are 0–400; t is 2–100; and R11 has the same meaning as previously defined.

The organosilicon composition can also have a structure defined by the formula:

Formula II

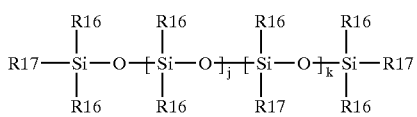

In Formula II, j is 1–5,000, and k is 0–100. R16 is an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; or an aralkyl group such as benzyl, phenylethyl, or 2-phenylpropyl.

R17 can be the same as R16, or R17 can consist of a structure such as

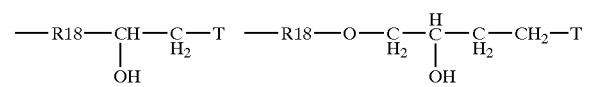

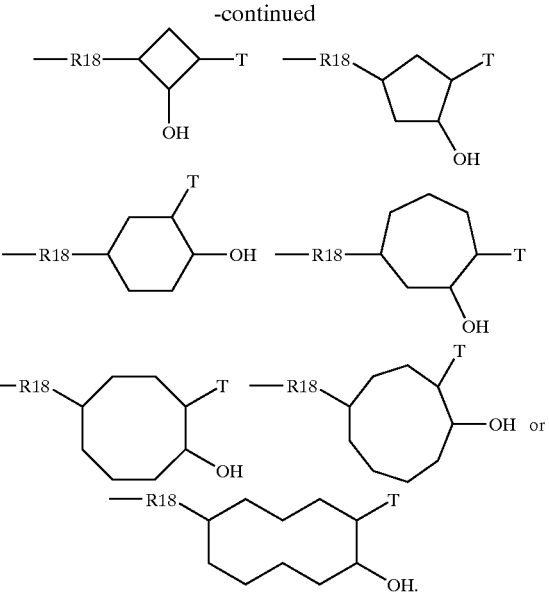

In these structures, R18 represents a divalent alkyl group such as methylene, ethylene, propylene, or butylene; a divalent aryl group such as phenylene, biphenylene, naphthylene, or anthracylene; a divalent alkaryl group such as tolylene or xylylene; or a divalent aralkyl group such as benzylene, phenylethylene, or 2-phenylpropylene.

It should be understood that in the ring structures shown above, while the T and OH groups must occupy adjacent sites, the R18 group can be attached to any remaining unoccupied site. As illustrated above, the various structure shown are merely representative of one of the arrangements possible.

T in these structures represents the group

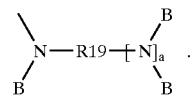

in which a is 1–20. The B group can be hydrogen; an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; or an aralkyl group such as benzyl, phenylethyl, or 2-phenylpropyl.

In addition, the B group can consist of structures such as

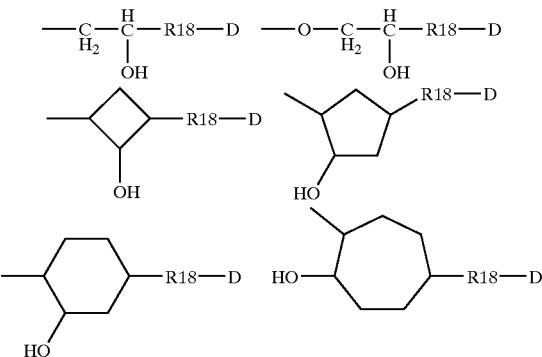

-continued

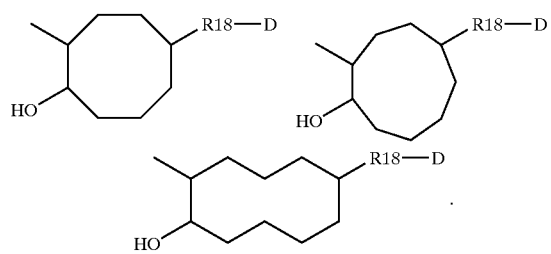

In these B groups, R18 is the same as previously defined. While the free site—and the OH group in the ring structures shown above must be located at adjacent positions on the ring, the R18-D group can be attached to the ring at any one of the remaining unoccupied positions, and the structures illustrated merely represent one of the arrangements possible.

The constituent D of the B group has the structure

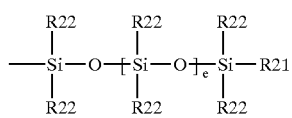

where e is 0–400. R21 can be an alkyl group such as methyl, ethyl, propyl, butyl, pentyl, hexyl or isobutyl; an aryl group such as phenyl, biphenyl, naphthyl, or anthracyl; an alkaryl group such as tolyl or xylyl; an aralkyl group such as benzyl, phenylethyl, or 2-phenylpropyl.

R21 can also occupy a D site, or R21 can further consist of a structure such as

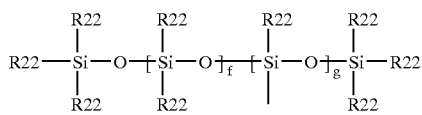

where f is 0–400, g is 2–100, and R22 is an alkyl group such as methyl, ethyl, propyl, butyl, pentyl, hexyl or isobutyl; an aryl group such as phenyl, biphenyl, naphthyl or anthracyl; an alkaryl group such as tolyl or xylyl; or an aralkyl group such as benzyl, phenylethyl or 2-phenylpropyl.

R19 in T is an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; or an aralkyl group such as benzyl, phenylethyl, or 2-phenylpropyl. Alternatively, R19 can consist of structures such as

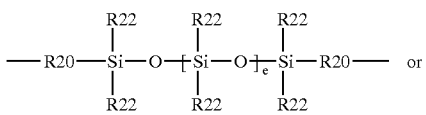

-continued

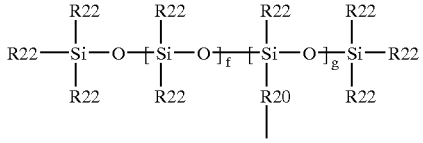

where e and f are 0–400, g is 2–100, and R22 is the same as previously defined.

R20 is an alkyl group such as methyl, ethyl, propyl, butyl, pentyl, hexyl, or isobutyl; an aryl group such as phenyl, biphenyl, naphthyl, or anthracyl; an alkaryl group such as tolyl or xylyl; an aralkyl group such as benzyl, phenylethyl, or 2-phenylpropyl; an alkyl amine group such as isobutyl ethylene amine; or oxygen.

Other variations may be made in the compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising the reaction product obtained by combining (i) an organic amine compound, (ii) an epoxy functional silicone containing at least two epoxy groups, (iii) water, (iv) a surfactant, and (v) an active ingredient selected from the group consisting of vitamins, drugs, antiperspirant salts, α-hydroxy acids, fragrances, and sunscreens, wherein the organic amine compound is selected from the group of ammonia, diethylene triamine, ethylene diamine, methane diamine, m-phenylene diamine; methylene dianiline, benzohydrazide, guanidine, benzidene sulfone, thioacetamide, piperazine, p-amino benzoic acid, thiosemicarbizide, allanturic acid, p,p'-thiodianiline, p-bromophenyl hydrazine, benzene pentamine, and N,N'-dimethyl ethylene diamine.

2. The composition of claim 1 wherein the epoxy functional silicone has the formula

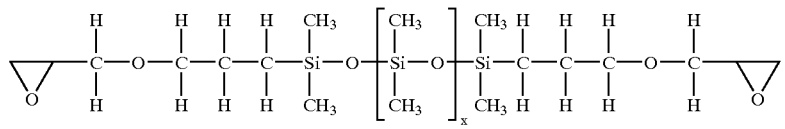

Epoxypropoxypropyl Terminated Polydimethylsiloxane where x is an integer having a value of 1 or more.

3. A composition comprising the reaction product obtained by combining (i) an organic amine compound, (ii) an epoxy functional silicone containing at least two epoxy groups, and (iii) a silicone fluid that is not reactive towards (i) and (ii).

4. The composition of claim 3 wherein the organic amine compound is selected from the group of ammonia, diethylene triamine, ethylene diamine, methane diamine, m-phenylene diamine, methylene dianiline, benzohydrazide, guanidine, benzidene sulfone, thioacetamide, piperazine, p-amino benzoic acid, thiosemicarbizide, allanturic acid, p,p'-thiodianiline, p-bromophenyl hydrazine, benzene pentamine, and N,N'-dimethyl ethylene diamine.

5. The composition of claim 3 wherein the epoxy functional silicone has the formula

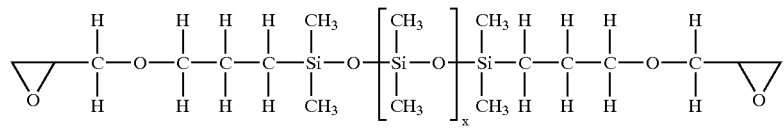

Epoxypropoxypropyl Terminated Polydimethylsiloxane where x is an integer having a value of 1 or more.

6. A composition according to claim 3 including (v) an active ingredient selected from the group consisting of vitamins, drugs, antiperspirant salts, α-hydroxy acids, fragrances, and sunscreens.

7. A composition according to claim 3 in which the silicone fluid (iii) is a volatile polydimethylsiloxane or a nonvolatile polydimethylsiloxane having a viscosity of 0.65–10,000 centistolce (mm²/s).

8. A silicone gel composition obtained by combining (i) an organic amine compound; (ii) an epoxy functional silicone containing at least two epoxy groups; and (iii) a polar organic compound or a nonpolar organic compound other than the organic compounds defined in (i), in which based on the total weight of (i)–(iii).

9. A composition according to claim 8 including (v) an active ingredient selected from the group consisting of vitamins, drugs, antiperspirant salts, α-hydroxy acids, fragrances, and sunscreens.

10. The composition of claim 8 wherein the organic amine compound is selected from the group of ammonia, diethylene triamine, ethylene diamine, methane diamine, m-phenylene diamine, methylene dianiline, benzohydrazide, guanidine, benzidene sulfone, thioacetamide, piperazine, p-amino benzoic acid, thiosemicarbizide, allanturic acid p,p'-thiodianiline, p-bromophenyl hydrazine, benzene pentamine, and N,N'-dimethyl ethylene diamine.

11. The composition of claim 8 wherein the epoxy functional silicone has the formula

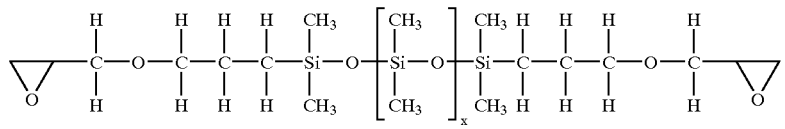

Epoxypropoxypropyl Terminated Polydimethylsiloxane where x is an integer having a value of 1 or more.

\* \* \* \* \*